(12) United States Patent
Palle et al.

(10) Patent No.: US 7,547,785 B2
(45) Date of Patent: Jun. 16, 2009

(54) PROCESS FOR PREPARING TOPOTECAN

(75) Inventors: Venkata Raghavendra Acharyulu Palle, Hyderabad (IN); Sekhar Munaswamy Nariyam, Hyderabad (IN); Lankeshwara Rao Matti, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 11/612,558

(22) Filed: Dec. 19, 2006

(65) Prior Publication Data

US 2007/0149783 A1    Jun. 28, 2007

Related U.S. Application Data

(60) Provisional application No. 60/747,881, filed on May 22, 2006.

(30) Foreign Application Priority Data

Dec. 26, 2005  (IN)  .................. 1919/CHE/2005

(51) Int. Cl.
*C07D 491/22*    (2006.01)
*C07D 491/147*    (2006.01)
(52) U.S. Cl. .......................................... 546/48; 546/47
(58) Field of Classification Search .................. 546/48, 546/47

See application file for complete search history.

(56) References Cited

U.S. PATENT DOCUMENTS

| 5,004,758 A | 4/1991 | Boehm et al. |
| 5,734,056 A | 3/1998 | Burk et al. |

FOREIGN PATENT DOCUMENTS

| EP | 0321122 A2 | 9/1996 |
| WO | WO 2005/046608 A2 * | 5/2005 |

* cited by examiner

*Primary Examiner*—Charanjit S Aulakh
(74) *Attorney, Agent, or Firm*—Robert A. Franks; Lee Banks; Anjum Swaroop (57) ABSTRACT

A process for preparing topotecan.

28 Claims, 7 Drawing Sheets

PROCESS FOR PREPARING TOPOTECAN

INTRODUCTION TO THE INVENTION

The present invention relates to a process for the preparation of topotecan, its salts and intermediates thereof. In an aspect, the invention relates to a process for the preparation of topotecan acetate of Formula V to avoid the formation of process related impurities and its conversion to topotecan hydrochloride.

Topotecan is chemically known as (S)-10-[(dimethylamino) methyl]-4-ethyl-4,9-dihydroxy-1H-pyrano[3',4':6,7]indolizino [1,2-b]quinoline-3,14-(4H,12H)-dione monohydrochloride (hereinafter referred to by the adopted name "topotecan hydrochloride") and is represented by structural Formula I Formula I Topotecan is a semi-synthetic derivative of camptothecin used for treatment of anti-tumor with topoisomerase I-inhibitory activity and is commercially available in the market under the brand name HYCAMTIN® for injection. Each vial contains topotecan hydrochloride equivalent to 4 mg of topotecan free base.

U.S. Pat. No. 5,004,758 and European Patent No. 0321122 B1 disclose topotecan, pharmaceutically acceptable salts, compositions containing topotecan and their use in the treatment of cancer. The patents also disclose a process for the preparation of topotecan hydrochloride.

U.S. Pat. No. 5,734,056 discloses a process for the preparation of topotecan hydrochloride and intermediates thereof, including preparing the tetrahydro camptothecin compound of Formula III by the hydrogenation of camptothecin of Formula II using $PtO_2$ in the presence of dimethyl sulfoxide (DMSO) and thiophene.

The foregoing processes suffer from serious disadvantages such as low yields of topotecan and use of excess amount of expensive reagents, rendering the processes unsuitable for industrial scale manufacturing.

There remains a need for a safe and efficient industrial scale process for preparing topotecan and its salts free of the above-mentioned problems.

SUMMARY OF THE INVENTION

The present relates to a process for the preparation of topotecan, its salts and intermediates thereof.

In one aspect the present invention relates to a process for the preparation of topotecan or salts thereof comprising:

i) hydrogenation of camptothecin of Formula II using a hydrogenation catalyst in the presence of thioanisole to afford tetrahydro camptothecin of Formula III;

ii) conversion of tetrahydro camptothecin of Formula III to a 10-hydroxy camptothecin of Formula IV by reacting with iodosobenzene diacetate;

iii) reacting the 10-hydroxy camptothecin of Formula IV with dimethyl amine and about 1 to about 3 equivalents of formaldehyde per equivalent of 10-hydroxy camptothecin in acetic acid to give topotecan acetate of Formula V; and iv) reacting topotecan acetate of Formula V with hydrochloric acid in presence of a suitable solvent to afford the topotecan hydrochloride compound of Formula I.

In a related aspect the present invention also provides a process for the purification of 10-hydroxy camptothecin compound of Formula IV to eliminate impurities comprising recrystallizing or slurrying in a suitable solvent.

In another aspect the present invention provides crystalline topotecan hydrochloride (the crystalline form hereinafter referred to as "Form I"), which is characterized by its X-ray powder diffraction ("XRPD") pattern and/or its differential scanning calorimetry ("DSC") curve.

An embodiment of the invention includes a process for preparing topotecan or a salt thereof, comprising reacting 10-hydroxy camptothecin with dimethylamine and about 1 to about 3 equivalents of formaldehyde, per equivalent of 10-hydroxy camptothecin, in the presence of acetic acid to form topotecan acetate.

Another embodiment of the invention includes a process for preparing topotecan or a salt thereof, comprising hydrogenating camptothecin in the presence of a hydrogenation catalyst and about 0.001 to about 0.1 molar equivalents of thioanisole per molar equivalent of camptothecin, to form 10-hydroxy camptothecin, reacting 10-hydroxy camptothecin with dimethylamine and about 1 to about 3 equivalents of formaldehyde, per equivalent of 10-hydroxy camptothecin, in the presence of acetic acid to form topotecan acetate, and reacting topotecan acetate with hydrochloric acid, to form topotecan hydrochloride.

A further embodiment of the invention includes topotecan hydrochloride having crystalline Form II.

DETAILED DESCRIPTION OF THE INVENTION

The present relates to a process for the preparation of topotecan, its salts and intermediates thereof.

In one aspect, the present invention relates to a process for the preparation of topotecan or salts thereof, comprising:

i) hydrogenating camptothecin of Formula II using a hydrogenation catalyst in the presence of thioanisole to afford tetrahydro camptothecin of Formula III;

Formula II

Formula III ii) converting tetrahydro camptothecin of Formula III to 10-hydroxy camptothecin of Formula IV by reacting with iodosobenzene diacetate;

Formula IV iii) reacting the 10-hydroxy camptothecin of Formula IV with dimethyl amine and about 1 to about 3 equivalents of formaldehyde per equivalent of 10-hydroxy camptothecin in acetic acid to give topotecan acetate of Formula V; and Formula V iv) reacting topotecan acetate of Formula V with hydrochloric acid in presence of a suitable solvent to afford topotecan hydrochloride of Formula I.

Step i) involves hydrogenating camptothecin of Formula II using a hydrogenation catalyst in the presence of thioanisole to afford tetrahydro camptothecin of Formula III.

The amount of thioanisole, which is used as catalyst moderator in the hydrogenation, can be from about 0.001 to about 1 molar equivalent per equivalent of the camptothecin of Formula II.

Hydrogenation catalysts which can be used in the formation of Formula III include but are not limited to metal catalysts such as platinum, platinum oxide, palladium, nickel and the like in the presence of hydrogen gas.

Suitably about 25 to about 100 pounds per square inch (psi), equivalent to about 2 Kg/cm$^2$ to about 7 Kg/cm$^2$, hydrogen gas pressure is used in the formation of tetrahydro camptothecin of Formula III.

The temperature for preparation of the tetrahydro camptothecin can range from about 20 to 120° C., or about 60 to 80° C., depending on the solvent used.

Tetrahydro camptothecin of Formula III obtained in step i) may or may not be isolated. It can be used in the form of an acetic acid solution directly in the next step to react with iodosobenzene diacetate.

Step ii) involves converting tetrahydro camptothecin of Formula III to 10-hyroxy camptothecin of Formula IV by reacting with iodosobenzene diacetate.

The quantity of iodosobenzene diacetate, which is used an oxidizing agent in step ii) can range form about 1.5 to about 3 molar equivalents, per equivalent of tetrahydro camptothecin of Formula III.

Suitable solvents that can be used in step ii) include without limitation thereto: water; organic acids such as acetic acid and the like; and alcohols such as methanol, ethanol, isopropyl alcohol, n-butanol and the like.

Suitably, the reaction of step ii) is carried out at temperatures from about 20 to about 120° C., or about 20 to about 40° C., for times sufficient to achieve reaction completion. Frequently, the time will be about 2 to 30 hours, or longer.

After completion of the reaction, the reaction mixture is concentrated and the product is isolated by crystallization.

10-hydroxy camptothecin obtained from the above process is optionally purified using suitable techniques such as recrystallization or slurrying in a suitable solvent.

In an embodiment, the purification process comprises:

a) providing a solution of 10-hydroxy camptothecin in a suitable solvent;

b) crystallizing the solid from solution of step i); and c) recovering the 10-hydroxy camptothecin in sufficiently pure form.

Step a) involves providing a solution of 10-hydroxy camptothecin in a suitable solvent.

The solution of 10-hydroxy camptothecin may be obtained by dissolving 10-hydroxy camptothecin in a suitable solvent, or such a solution may be obtained directly from a reaction in which 10-hydroxy camptothecine is formed.

Suitable solvents, which can be used in the providing solution, include but are not limited to N,N-dimethylformamide (DMF), dimethylsulfoxide (DMSO) and the like.

The temperatures for preparation of the solution can range from about 20 to 120° C., or to about 60 to about 80° C., depending on the solvent used. Any other temperature is also acceptable as long as the stability of 10-hydroxy camptothecin is not compromised.

The quantity of solvent used for preparing the solution depends on the nature of solvent and the temperature adopted for preparing the solution. The concentration of 10-hydroxy camptothecin in the solution may generally range from about 0.1 to about 10 g/ml in the solvent.

Step b) involves crystallizing the solid from solution of step i).

For crystallization to occur, the solution may be maintained further at temperatures lower than the dissolution temperatures such as for example below about 10° C. to about 35° C., for a period of time as required for a more complete isolation of the product. The exact cooling temperature and time required for complete isolation can be readily determined by a person skilled in the art and will also depend on parameters such as concentration and temperature of the solution or slurry.

Optionally, isolation may be enhanced by methods such as cooling, partial removal of the solvent from the mixture, seeding, adding an anti-solvent to the reaction mixture, or a combination thereof.

Suitable anti-solvents which can be used in the recovering pure solid of 10-hydroxy camptothecin of Formula IV include but are not limited to: alcohols such as methanol, ethanol, isopropyl alcohol, 1-propanol, n-butanol and the like; and ketones such as acetone, methyl isobutyl ketone, methyl tertiary butyl ketone, and the like.

Step c) involves recovering the 10-hydroxy camptothecin in sufficiently pure form.

The solid can be recovered by using any techniques such as filtration by gravity or by suction, centrifugation, decantation, and the like.

The obtained wet cake optionally can be slurred in a suitable solvent to remove non-volatile components.

Suitable solvents that can be used in providing a slurry include without limitation thereto alcohols such as methanol, ethanol, isopropyl alcohol, 1-propanol, n-butanol and the like.

The wet cake thus obtained may optionally be further dried. Drying can be suitably carried out in a tray dryer, vacuum oven, air oven, fluidized bed drier, spin flash dryer, flash dryer and the like. The drying can be carried out at temperatures of about 35° C. to about 100° C. The drying can be carried out for any desired time periods from about 1 to 20 hours, or longer, until a desired purity has been obtained.

The purity of the compound of 10-hydroxy camptothecin that is obtained from present invention frequently is greater than or equal to about 95%, or from about 95 to 98%, as determined by high performance liquid chromatography (HPLC). Repeating the above purification process can further enhance the purity.

Step iii) involves reacting the 10-hydroxy camptothecin of Formula IV with dimethyl amine and about 1 to about 3 equivalents of formaldehyde per equivalent of 10-hydroxy camptothecin in acetic acid to give topotecan acetate of Formula V.

The amount of dimethyl amine, which is used in the preparation of topotecan acetate of Formula V can range from about 2 to about 6 molar equivalents per mole of 10-hydroxy camptothecin of Formula IV.

Dimethyl amine can be used in the form of a gas or a solution in water or an organic solvent. In an embodiment, dimethyl amine is used in the form of an aqueous solution having a concentration ranging from about 35 to about 45% w/w.

The amount of formaldehyde that is used in the preparation of topotecan acetate of Formula V is about 1 to about 3 molar equivalents with respect to 10-hydroxy camptothecin of Formula IV. In an embodiment the amount of formaldehyde is about 1 to about 2 molar equivalents, per molar equivalent of 10-hydroxy camptothecin. In another embodiment, the quantity of formaldehyde is about 1.3 molar equivalents, per molar equivalent of 10-hydroxy camptothecin.

Suitably, formaldehyde is used in the form of an aqueous solution having a concentration ranging form about 35 to about 40% w/w. However, other concentrations are useful.

The process for preparing topotecan acetate of step iii) can be carried out suitably at temperatures from about 30 to about 60° C., for a time sufficient to achieve reaction completion. This frequently will require about 1 to about 10 hours, or longer.

After completion of the reaction topotecan acetate can be isolated from the reaction mixture by adding a suitable anti-solvent or by adding the reaction mixture to the anti-solvent.

Suitable anti-solvents that can be used in the isolation of topotecan acetate include without limitation thereto ketones like acetone, methyl ethyl ketone, methyl isobutyl ketone, methyl tertiary butyl ketone, and the like and combination thereof.

The solid obtained can be recovered by any conventional techniques such as filtering, decanting, centrifuging and the like.

Topotecan acetate provided by the process of this invention is substantially free of its structural and process related impurities and has a purity greater than or equal to about 98% as measured by HPLC.

Step iv) involves reacting topotecan acetate of Formula V with hydrochloric acid in presence of a suitable solvent to afford topotecan hydrochloride of Formula I.

Suitable solvents that can be used in the preparation of topotecan hydrochloride include but are not limited to: water; alcohols such as methanol, ethanol, isopropyl alcohol and the like; and combinations thereof.

Hydrochloric acid that can be used in the present invention includes hydrochloric acid gas, aqueous hydrochloric acid, methanolic hydrochloride, isopropanolic hydrochloride, ethyl acetate hydrochloride and the like. In one embodiment hydrochloric acid is used in the form of an aqueous solution.

The reaction for preparing topotecan hydrochloride of step iv) can be carried out at temperatures from about 20 to about 70° C., or from about 20 to about 50° C.

After completion of the reaction, the reaction solution is concentrated to a minimum volume and then the solid can be precipitated by adding an anti-solvent.

Reaction solution is concentrated until the concentration of the solute is from about 0.02 to about 0.1 g/ml.

Suitable anti-solvents which can be used for solid precipitation include but are not limited to: ketone solvents such as acetone, methyl ethyl ketone, methyl isobutyl ketone, methyl tertiary-butyl ketone, and the like; hydrocarbons such as n-hexane, cyclohexane, heptane, and the like; chlorinated solvents such dichloromethane, chloroform and the like; and esters such as ethyl acetate, ethyl aceto acetate, and the like.

The solid thus obtained can be recovered by conventional techniques such as filtering, decanting, centrifuging and the like.

Topotecan hydrochloride obtained in step iv) is optionally slurried in a suitable ketone solvent such as acetone, methyl ethyl ketone, methyl isobutyl ketone, methyl tertiary butyl ketone, and the like to afford a free flowing solid.

Topotecan hydrochloride and its intermediates may optionally be further dried. Drying can be suitably carried out in a tray dryer, vacuum oven, air oven, fluidized bed drier, spin flash dryer, flash dryer and the like. The drying can be carried out at reduced pressures, such as below about 750 mm Hg or below about 50 mm Hg, at temperatures such as about 35° C. to about 100° C. The drying can be carried out for any desired time periods to achieve a desired purity, such as from about 1 to about 20 hours.

Topotecan acetate can also be converted to other desired pharmaceutically acceptable acid addition salts using other suitable acids by following a similar procedure.

Suitable pharmaceutically acceptable acids which can be used include, but are not limited to: inorganic acids such as hydrochloric acid, hydrobromic acid, hydroiodic acid; and organic acids such as acetic acid, tartaric acid, oxalic acid, and the like.

Yet another aspect of the present invention provides crystalline topotecan hydrochloride Form I, provided by the above described process, characterized by its X-ray powder diffraction ("XRPD") pattern and/or its differential scanning calorimetry ("DSC") curve.

Figure 1:
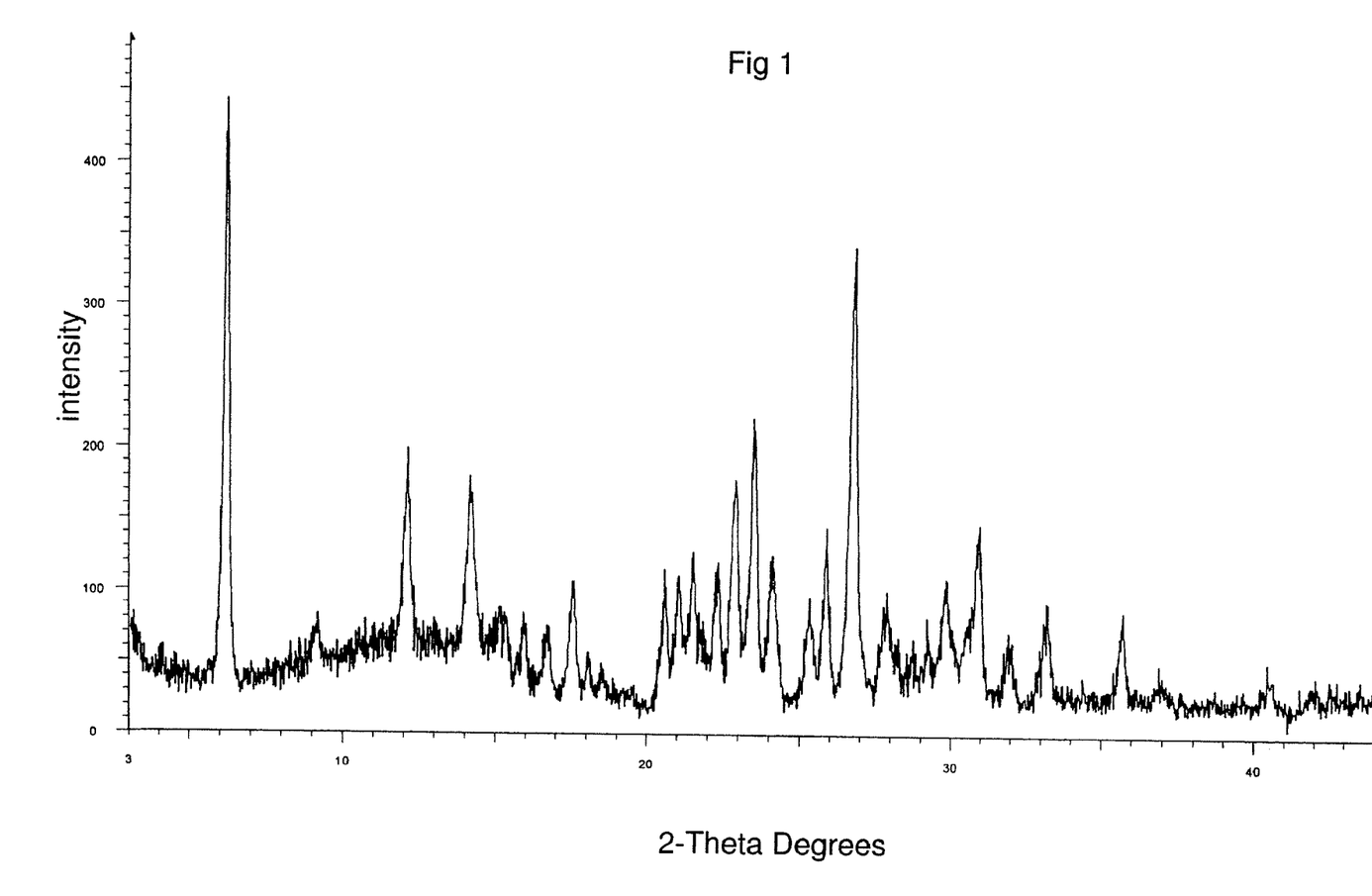
FIG. 1 is an X-ray powder diffraction pattern of topotecan hydrochloride crystalline Form I prepared according to Example 3.

Crystalline topotecan hydrochloride Form I obtained in the process of present invention is characterized by its XRPD pattern, substantially in accordance with the pattern of FIG. 1. All XRPD data reported herein were obtained using Cu Kα radiation, having the wavelength 1.541 Å and were obtained using a Bruker Axe D8 Advance Powder X-ray Diffractometer.

Crystalline topotecan hydrochloride Form I is characterized by an XRPD diffraction pattern comprising characteristic peaks approximately at about 6.1, 12.1, 14.2, 22.9, 23.5, and 26.8, ±0.2 degrees two theta.

Differential scanning calorimetric analysis was carried out in a DSC Q1000 model from TA Instruments with a ramp of 5° C./minute with a modulation time of 60 seconds and a modulation temperature of ±1° C. The starting temperature was 0° C. and ending temperature was 200° C.

Figure 2:
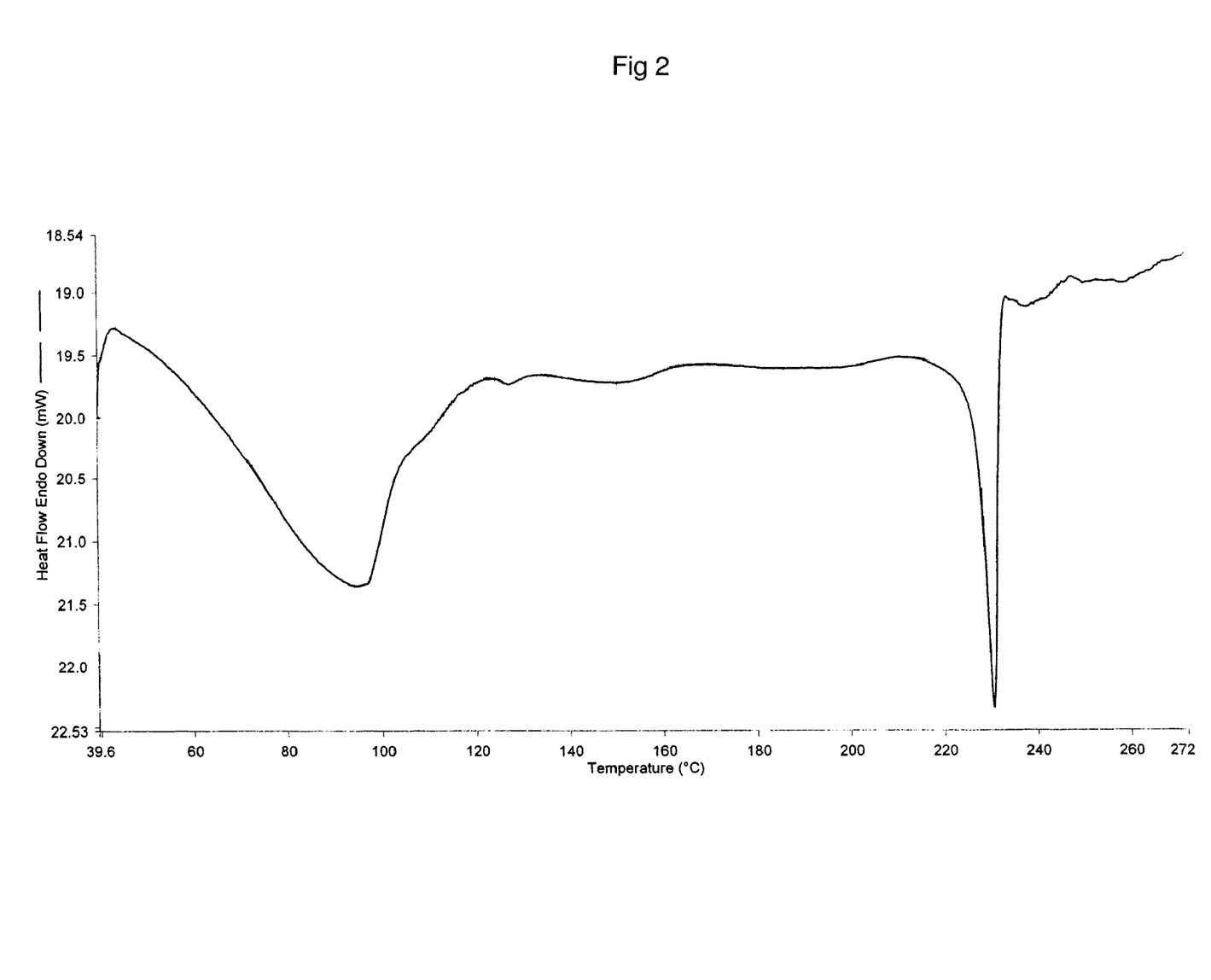
FIG. 2 is a differential scanning calorimetry curve of topotecan hydrochloride crystalline Form I prepared according to Example 3.

Crystalline topotecan hydrochloride Form I of the present invention has a characteristic differential scanning calorimetric curve substantially in accordance with FIG. 2, having endothermic peaks at about 94° C., 151° C., and 231° C.

Figure 3:
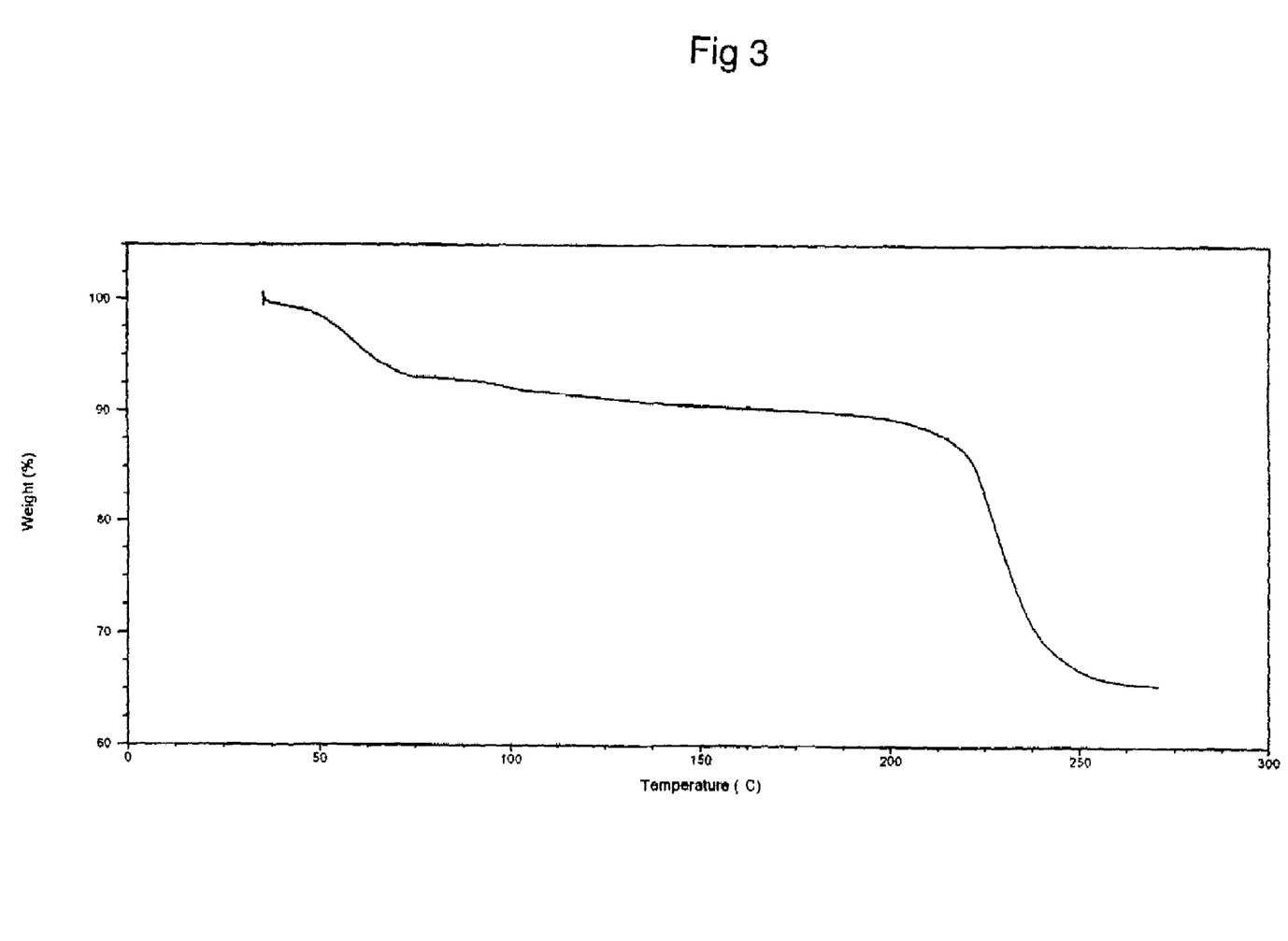
FIG. 3 is a thermogravimetric analysis curve of topotecan hydrochloride crystalline Form I prepared according to Example 3.

Crystalline topotecan hydrochloride Form I of the present invention has a characteristic termogravimetric curve (TGA) corresponding to a weight loss of about 9.7% w/w substantially in accordance with FIG. 3.

In a related embodiment the present invention also provides an alternate process for the purification of topotecan hydrochloride comprising:

a) providing a solution of topotecan hydrochloride in water;

b) removing the water from the solution of step a) by co-distilling with a suitable solvent; and c) recovering pure topotecan hydrochloride of Formula I.

Step a) involves providing a solution of topotecan hydrochloride in water;

The solution of topotecan hydrochloride can be obtained by dissolving the compound in water or from a previous processing step. Any form of topotecan hydrochloride is acceptable for preparation of the solution, such as any crystalline or amorphous form of topotecan hydrochloride.

The concentration of topotecan hydrochloride in the solution is not critical as long as sufficient water is employed to ensure total dissolution. The amount of water employed is kept small so as to avoid excessive product loss during crystallization and isolation. The quantity of water used for providing solution of topotecan hydrochloride can range from about 3 times to about 20 times the weight of topotecan hydrochloride.

The solution can be prepared at temperatures ranging from about 25° C. to 100° C. Depending on the quantity of solvent taken, it may dissolve at 25 to 100° C., or the solution may need to be heated to elevated temperatures of about 50° C. to 100° C.

The solution can be optionally treated with activated charcoal to enhance the color of the compound followed by filtration through a medium such as through a flux calcined diatomaceous earth (Hyflow) bed to remove the carbon.

The carbon treatment can be given either at the dissolution temperatures or after cooling the solution to lower temperatures.

The solution can optionally be filtered by passing through paper, glass fiber, or other membrane material or a clarifying agent such as Hyflow. Depending upon the equipment used and the concentration and temperature of the solution, the filtration apparatus may need to be preheated to avoid premature crystallization.

Step b) involves removing the water from solution of step a) by co-distilling with a suitable organic solvent;

Suitable organic solvents for co-distillation in step b) include but are not limited to alcohols such as methanol, ethanol, isopropyl alcohol, 1-propanol and the like.

Water can be removed suitably by using evaporation, atmospheric distillation or distillation under vacuum.

Distillation of water may be conducted under a vacuum of about 100 mm Hg to about 600 mm Hg at temperatures of about 40° C. to about 70° C. Any temperature and vacuum conditions can be used as long as concentration occurs without an increase in the impurity levels.

The co-distillation process can be repeated until most of the water is removed from the mixture and from about 5 to about 15 ml of the organic solvent remains, per gram of topotecan hydrochloride in the solution.

The resultant solution can then be stirred at a suitable lower temperature such as room temperature for times such as about 30 minutes to about 5 hours, or longer, to precipitate the solid.

Step c) involves recovering the pure topotecan hydrochloride of Formula I.

The solid can be recovered by conventional techniques such as filtering, decanting, centrifuging and the like.

The wet cake obtained in step c) may optionally be further dried. Drying can be suitably carried out in a tray dryer, vacuum oven, air oven, fluidized bed drier, spin flash dryer, flash dryer and the like. The drying can be carried out at temperatures of about 35° C. to about 70° C. The drying can be carried out for any desired time periods until the desired product purity is achieved, times from about 1 to 20 hours, or longer, frequently being sufficient.

Topotecan hydrochloride obtained from step c) is characterized by an XRPD diffraction pattern comprising characteristic peaks at about 7.4, 7.9, 10.1, 19.7, 24.0, 25.0, 25.9, 27.1, and 27.9, ±0.2 degrees two theta (this crystalline form being hereinafter referred to as "Form II"). Crystalline topotecan hydrochloride Form II of the present invention has a characteristic X-ray powder diffraction pattern substantially in accordance with FIG. 4.

Figure 5:
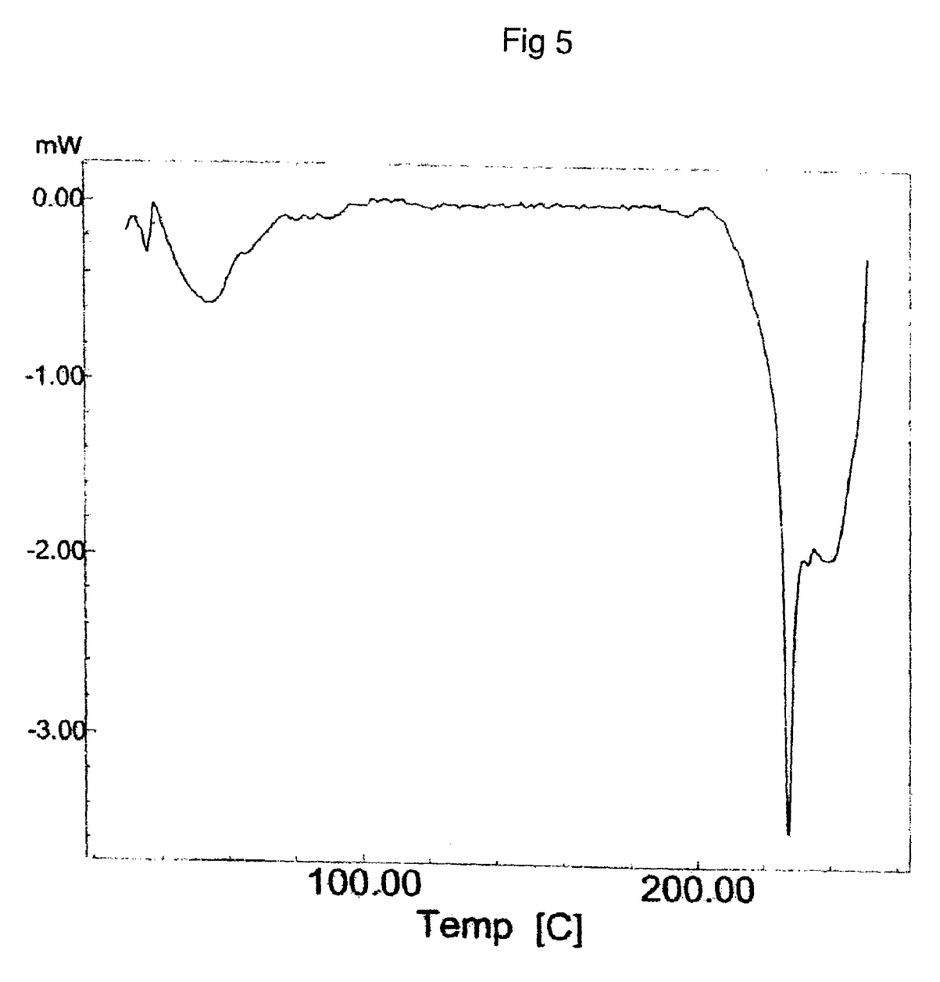
FIG. 5 is a differential scanning calorimetry curve of topotecan hydrochloride crystalline Form II prepared according to Example 4.

Crystalline topotecan hydrochloride Form II of the present invention has a characteristic differential scanning calorimetric curve substantially in accordance with FIG. 5. Crystalline topotecan hydrochloride Form II of the present invention has a characteristic differential scanning calorimetric curve having an endothermic peak at about 228° C. (onset about 225° C. and endset about 231° C.).

Figure 6:
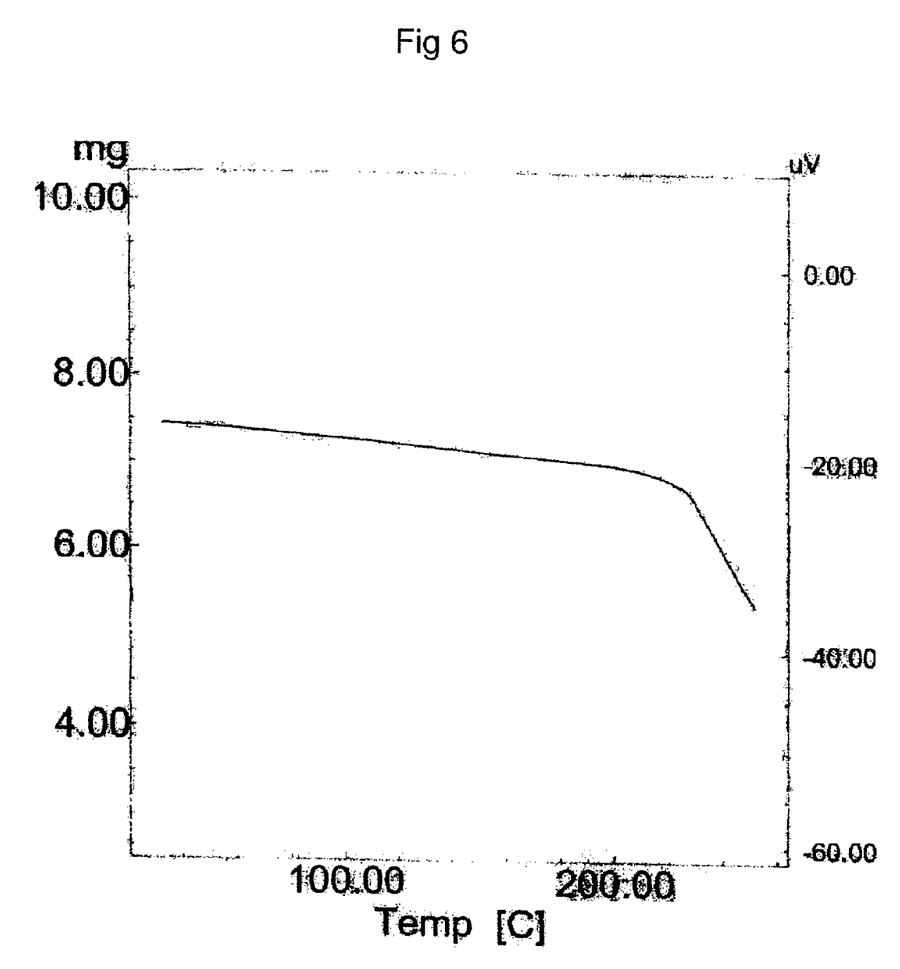
FIG. 6 is a thermogravimetric analysis curve of topotecan hydrochloride crystalline Form II prepared according to Example 4.
Figure 7:
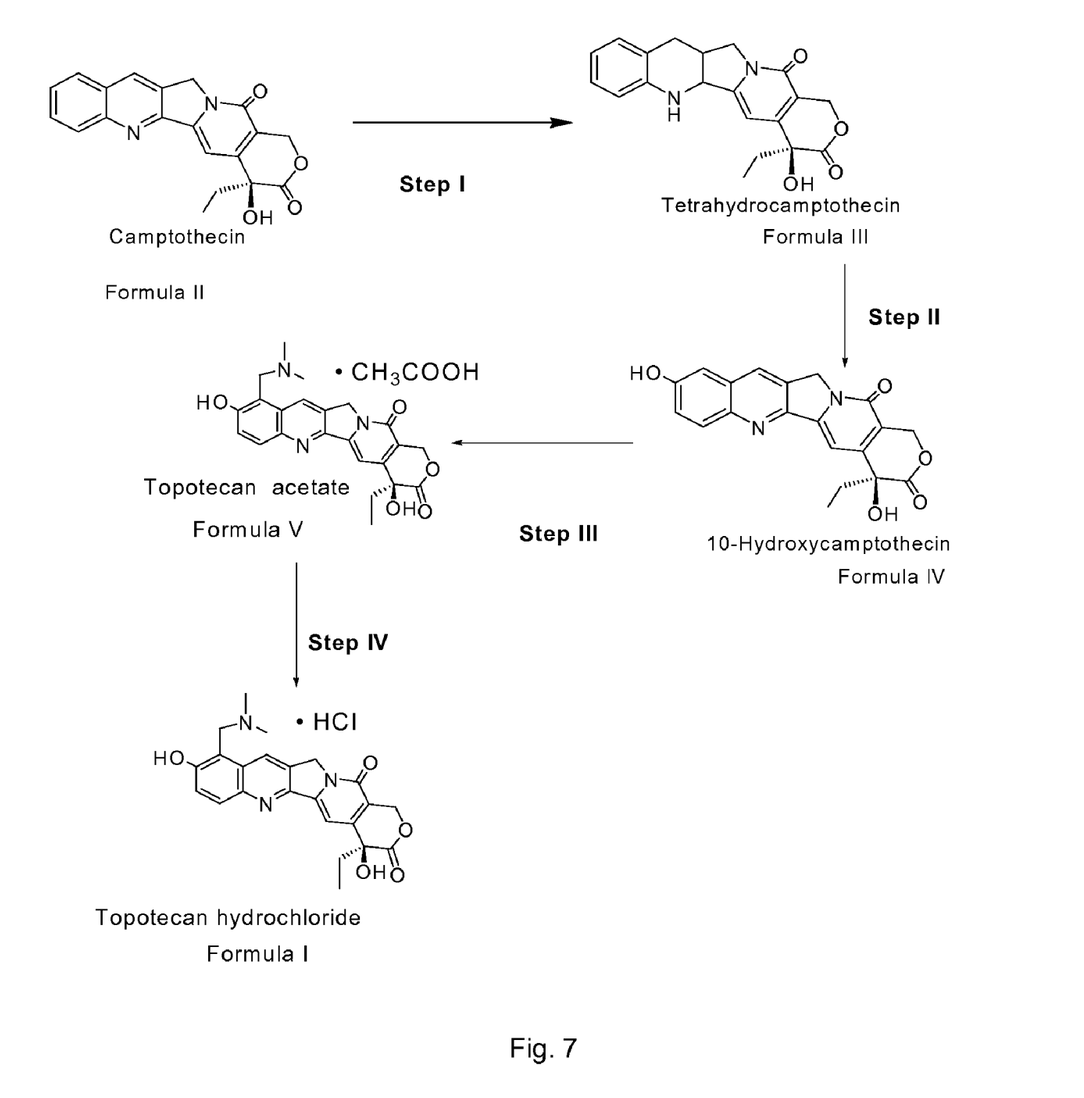
FIG. 7 is a schematic representation of a process for preparing topotecan hydrochloride.

Crystalline topotecan hydrochloride of Form II of the present invention has a characteristic termogravimetric curve (TGA) corresponding to a weight loss of about 3% w/w, substantially in accordance with FIG. 6.

Topotecan hydrochloride of Formula I, provided by the process of this invention has a purity by high performance liquid chromatography ("HPLC") greater than or equal to about 99.5%. It has low levels of any one or more impurities. For example it contains less than about 0.15%, or less than about 0.04%, by weight of (S)-4-ethyl-4-hydroxy-1H-pyrano[3',4':6,7]indolino(1,2-b)quinoline-3,14-(4H,12H)-dione of Formula II ("Impurity A");

Formula II less than about 0.15%, or less than about 0.08%, by weight of (S)-4-ethyl-4,9-dihydroxy-1H-pyrano[3',4':6,7]indolino(1,2-b)quinoline-3,14-(4H,12H)-dione of Formula IV ("Impurity B");

Formula IV about 0.001% to about 0.15% by weight of (S)-10-[(dimethylamino)methyl]-4-ethyl-4,9-dihydroxy-12-methylene-1,12-dihydro-4H-2-oxa-6,12a-diaza-dibenzo[b,h]fluorene-3,13-dione of Formula VI ("Impurity C"); and Formula VI less than about 0.15% by weight of 2-(1-Dimethylaminomethyl-2-hydroxy-8-hydroxymethyl-9-oxo-9,11-dihydro-indolizino[1,2-b]quinolin-7-yl)-2-hydroxy-butyric acid of Formula VII ("Impurity D")

Formula VII

Topotecan hydrochloride obtained by the above process has been analyzed using high performance liquid chromatography ("HPLC") with the conditions described in Table 1.

TABLE 1

| Column and Packing: | Intertsil ODS 3V, 150 × 4.6 mm, 5 μm |
|---|---|
| Buffer | 1.36 g of potassium dihydrogen phosphate in 1000 ml of water and adjusted to pH 3.0 ± 0.05 with phosphoric acid. |
| Mobile Phase A: | Used buffer as Mobile phase A |
| Mobile Phase B: | Filtered and degassed acetonitrile. |

| Gradient: | Time (minutes) | Solution A (% v/v) | Solution B (% v/v) | Elution |
|---|---|---|---|---|
| | 0 | 90 | 10 | Isocratic |
| | 11 | 90 | 10 | Linear gradient |
| | 30 | 70 | 30 | Linear gradient |
| | 40 | 50 | 50 | Linear gradient |
| | 41 | 90 | 10 | Re-equilibration |
| | 50 | 90 | 10 | Equilibration |

| Flow rate: | 1.0 ml/minute |
|---|---|
| Wavelength of detection: | 267 nm by UV |
| Temperature: | 25 ± 2° C. |
| Injection volume: | 20 μL |
| Diluent: | Mixed buffer: Acetonitrile in the ratio of 85:15 (% v/v) |
| Run time: | 50 minutes |

The relative retention times ("RRT") of impurity peaks are given below, where topotecan is assigned the value of 1.

| Impurity | RRT |
|---|---|
| Topotecan | 1.00 |
| Impurity A | 1.72 |
| Impurity B | 1.46 |
| Impurity C | 1.28 |
| Impurity D | 0.88 |

In an embodiment, topotecan hydrochloride obtained by the process of present invention has a particle size of $D_{10}$ less than about 10 microns, $D_{50}$ less than about 50 microns, and $D_{90}$ less than about 100 microns.

The $D_{10}$, $D_{50}$ and $D_{90}$ values are useful ways for indicating a particle size distribution. $D_{90}$ refers to the value for the particle size for which at least 90 volume percent of the particles have a size smaller than the value given. Likewise $D_{50}$ and $D_{10}$ refer to the values for the particle size for which 50 volume percent, and 10 volume percent, respectively, of the particles have a size smaller than the value given. Methods for determining $D_{10}$, $D_{50}$ and $D_{90}$ include laser light diffraction, such as using equipment from Malvern Instruments Ltd. (of Malvern, Worcestershire, United Kingdom). There is no specific lower limit for any of the D values.

Topotecan hydrochloride obtained using the process of the present invention has a residual solvent content that is within the limits given by the International Conference on Harmonization of Technical Requirements for Registration of Pharmaceuticals for Human Use ("ICH") guidelines. The guideline solvent level depends on the type of solvent but is not more than about 5000 ppm, or about 4000 ppm, or about 3000 ppm.

Topotecan hydrochloride obtained in this invention contains less than about 100 ppm or less than about 500 ppm of methanol, less than about 100 ppm or less than about 500 ppm of isopropyl alcohol, less than about 100 ppm or less than about 500 ppm of acetone, less than about 100 ppm or less than about 500 ppm of 1-propanol, and less than about 100 ppm or less than about 500 ppm of N,N-dimethylformamide.

Certain specific aspects and embodiments of the invention will be explained in more detail with reference to the following examples, which are provided by way of illustration only and should not be construed as limiting the scope of the invention in any manner.

EXAMPLE 1

Preparation of 10-Hydroxy Camptothecin

6 L of acetic acid and 60 ml of thioanisole were taken into a reactor and there was charged 2 Kg of camptothecin suspended in 6 L of acetic acid. 666 g of platinum oxide was suspended in 6 L of acetic acid in another container and then the suspension was charged to the reactor at 27.5° C. The container was washed with 2 L of acetic acid and then charged into above reactor. The obtained reaction mixture was subjected to evacuation and then a pressure of 45 psi was applied using hydrogen gas, which was then slowly increased to 65 psi at 34.3° C. and the mixture was stirred for 10 minutes. The reaction mixture was heated to 61.9° C. and stirred for 6 hours at 63.7° C. and at 64 psi. Then the reaction mass was allowed to cool to 41.3° C. with stirring for 22 hours at 62 psi. Reaction completion was confirmed by thin layer chromatography ("TLC"). After completion of the reaction, the hydrogen pressure was slowly released and the reactor was flushed with nitrogen gas. Then the reaction mixture was filtered through a Hyflow bed followed by washing with 6.6 L of acetic acid.

26.6 L of water was added to the filtrate containing tetrahydro camptothecin compound of Formula III. 4 Kg of iodosobenzene diacetate was added to the above solution and subjected to stirring for about 18 hours at 27.5° C. The reaction mixture was distilled at 115° C. until 13 L of solvent remained (distillate quantity 41.5 L). The reaction mixture was allowed to cool to 27.9° C. Then the reaction suspension was filtered and the wet solid washed with 4 L of methanol.

The resultant wet solid and 12 L of dimethylformamide were charged into a flask and the suspension was subjected to heating to 76.3° C. The suspension was stirred for 20 minutes for complete dissolution at 76.3° C. and the obtained solution was stirred for 1 hour at 76.5° C. The solution was allowed to cool to 27.5° C. and 52.5 L of methanol was charged and then subjected to stirring for about 5 hours at 27.5° C. The mass was filtered and washed with methanol followed by suction drying. The wet material was transferred into a flask and 6 L of methanol was charged, followed by raising the temperature to 62.5° C. and maintaining at the same conditions for about 1 hour. The mass was cooled to 27.5° C. and then the solid was filtered. The flask was rinsed with 3 L of methanol and then the wet solid was washed with the above rinsing. The obtained solid was suction dried and dried at 57.8° C. under high vacuum at 680 mm Hg for 12 hours to afford 1070 g of the title compound having a purity of about 97.4% by HPLC.

EXAMPLE 2

Preparation of Topotecan Acetate of Formula V 0.3 Kg of 10-hydroxy camptothecin (Formula IV) prepared according to Example-1 was suspended in 6 L of acetic acid and stirred for 5 minutes. The obtained solution was charged into a reactor and stirred for 20 minutes. 0.51 L of a 40% aqueous solution of dimethyl amine and 0.078 L of a 37% of aqueous solution of formaldehyde were charged into the reactor, the temperature raised to 45.3° C. and the reaction mixture stirred for 2 hours at 45.3° C. The reaction solution was allowed to cool to 34.8° C. and then cooled to 27.5° C. 42 L of acetone was charged into above reaction solution and stirred for 1 hour at 27.5° C. for complete precipitation. The formed solid was filtered and the reactor rinsed with 1.5 L of acetone. The wet solid was washed with the rinsing and then washed with 0.3 L of 1-propanol. The resultant solid was suction dried for 20 minutes and then dried for 5 hours at 52° C. under a vacuum of 690 mm Hg to afford 330 g of title compound having a purity by HPLC of about 98.9%.

EXAMPLE 3

Preparation of Topotecan Hydrochloride (Formula I)

8.7 L of water and 78 ml of 0.1 N hydrochloric acid were charged into a reactor and stirred for 15 minutes. 250 g of topotecan acetate prepared according to Example 2 was charged into the above reactor and stirred for 15 minutes. The obtained solution was filtered through a 0.22-micron filter. The filtrate and 8.8 L of isopropyl alcohol were charged into a flask and concentrated at 35.8° C. under a vacuum of −0.95 $Kg/cm^2$ until 5 L of the solvent remained (distillate quantity 10.5 L). Then the reaction mass was cooled to 27° C. and 50 L of acetone charged. The obtained suspension was stirred for 1 hour at 27° C. and then filtered. The flask was rinsed with 2 L of acetone and the wet solid was washed with the rinsing. The wet solid was suction dried for 30 minutes and then wet solid was suspended in 9 L of acetone in a reactor and stirred for 30 minutes at 26.8° C. The suspension was filtered and the reactor rinsed with 5 L of acetone. The wet solid was washed with the rinsing and then solid was suction dried for 30 minutes. The obtained wet solid was dried at 28° C. under a vacuum of 700 mm Hg for 5 hours with de-lumping of the solid every hour of the drying. Finally the resultant solid was dried at 48° C. under a vacuum of 700 mm Hg for 1 hour to afford 169 g of the title compound of Formula I.

Purity by HPLC: 99.65%

Impurity A: less than 0.009%

Impurity B: less than 0.001%

Impurity C: 0.04% (limit of detection 0.001%).

Particle size distribution:

$D_{10}$=1.69 microns $D_{50}$=9.40 microns $D_{90}$=33.3 microns.

EXAMPLE 4

Purification of Topotecan Hydrochloride (Formula I)

8 g of topotecan hydrochloride and 80 ml of water were charged into a round bottom flask and stirred for 10 minutes. The solution was filtered trough a flux calcined diatomaceous earth ("Hyflow") bed and the Hyflow bed was washed with 40 ml of water. The filtrate was distilled under vacuum at 680 mm Hg until 60 ml of solvent remained. 120 ml of 1-propanol was charged into above obtained solution and distilled under a vacuum of 680 mm Hg at 47° C. until 120 ml of solvent remained. 120 ml of 1-propanol was charged into obtained solution followed by concentration under vacuum of 680 mm Hg at 47° C. until 120 ml of solvent remained. The above said step was repeated two more times and then the solution was cooled to 25° C. and 40 ml of 1-propanol was charged into the obtained solution. The resultant suspension was stirred for 60 minutes at 27° C., filtered, and the solid washed with 16 ml of 1-propanol and finally dried at 47° C. under a vacuum of 680 mm Hg to afford the title compound having crystalline Form II.

Purity by HPLC: 99.94%.
Water content by Karl Fisher method: 7.1% w/w.

The invention claimed is:

1. A process for preparing topotecan or a salt thereof, comprising the steps of:
   hydrogenating camptothecin in the presence of a hydrogenation catalyst and thioanisole to form 10-hydroxy-camptothecin; and
   reacting 10-hydroxy camptothecin with dimethylamine and about 1 to about 3 equivalents of formaldehyde, per equivalent of 10-hydroxy camptothecin, in the presence of acetic acid to form topotecan acetate.

2. The process of claim 1, wherein reaction is conducted using about 1 to about 2 equivalents of formaldehyde, per equivalent of 10-hydroxy camptothecin.

3. The process of claim 1, wherein reaction is conducted using about 1.3 equivalents of formaldehyde, per equivalent of 10-hydroxy camptothecin.

4. The process of claim 1, wherein topotecan acetate is isolated by adding an antisolvent.

5. The process of claim 1, further comprising reacting topotecan acetate with hydrochloric acid, to form topotecan hydrochloride.

6. The process of claim 5, further comprising crystallizing topotecan hydrochloride by adding an antisolvent to a solution of topotecan hydrochloride.

7. The process of claim 6, wherein an antisolvent comprises a ketone, a hydrocarbon, a chlorinated solvent, or an ester.

8. The process of claim 6, wherein an antisolvent comprises a ketone.

9. The process of claim 6, wherein an antisolvent comprises acetone.

10. The process of claim 1, wherein topotecan or a salt thereof contains about 0.001% to about 0.15% by weight of a compound having a formula:

11. A process for preparing topotecan or a salt thereof, comprising hydrogenating camptothecin in the presence of a hydrogenation catalyst and about 0.001 to about 0.1 molar equivalents of thioanisole per molar equivalent of camptothecin, to form 10-hydroxy camptothecin, reacting 10-hydroxy camptothecin with dimethylamine and about 1 to about 3 equivalents of formaldehyde, per equivalent of 10-hydroxy camptothecin, in the presence of acetic acid to form topotecan acetate, and reacting topotecan acetate with hydrochloric acid, to form topotecan hydrochloride.

12. The process of claim 11, wherein reacting 10-hydroxy camptothecin is conducted using about 1 to about 2 equivalents of formaldehyde, per equivalent of 10-hydroxy camptothecin.

13. The process of claim 11, wherein reacting 10-hydroxy camptothecin is conducted using about 1.3 equivalents of formaldehyde, per equivalent of 10-hydroxy camptothecin.

14. The process of claim 11, further comprising crystallizing topotecan hydrochloride by adding an antisolvent to a solution of topotecan hydrochloride.

15. Crystalline topotecan hydrochloride having an X-ray power diffraction pattern comprising characteristic peaks at about 7.9, 24.0, 25.0, and 27.9 ±0.2 degrees 2 theta.

Figure 4:
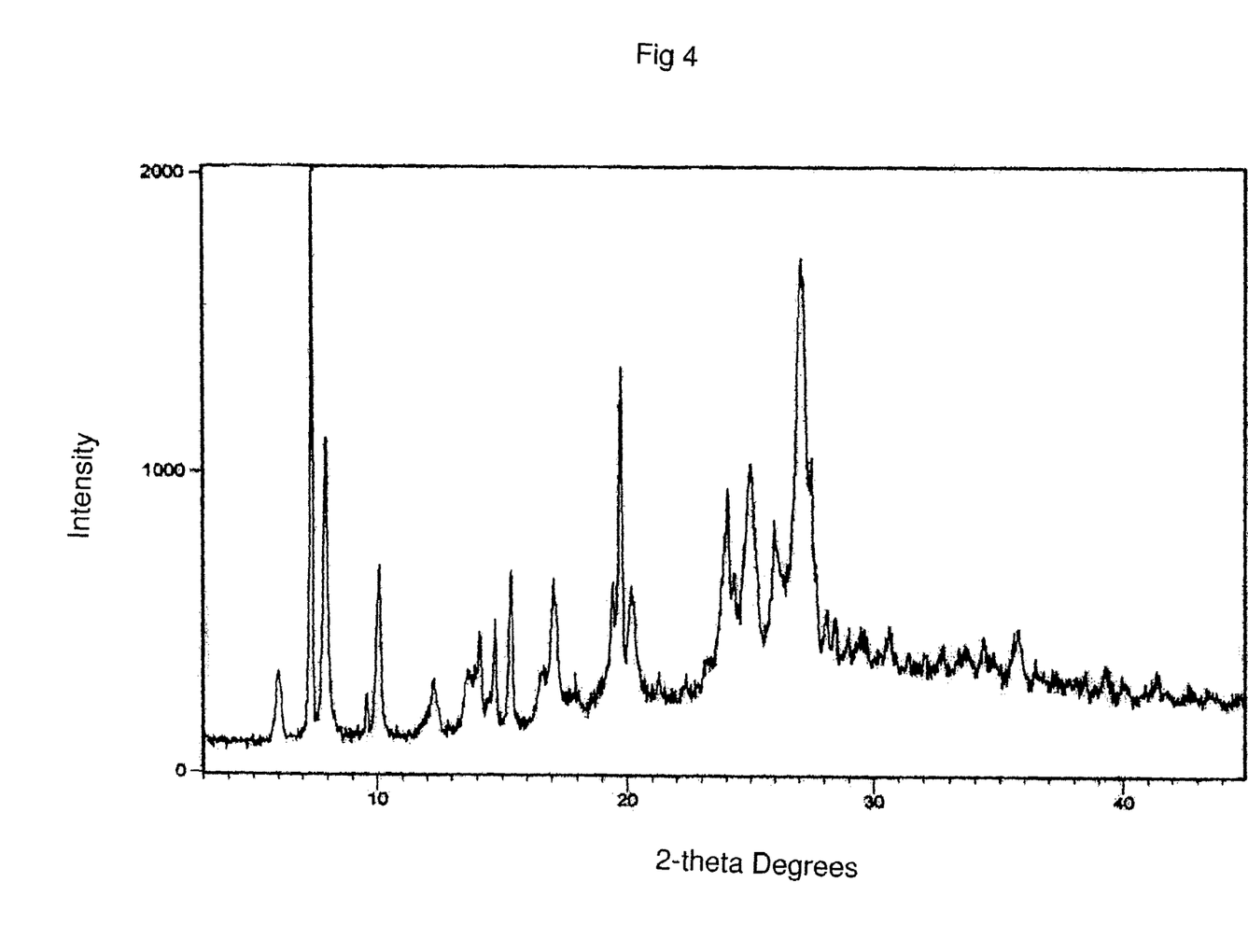
FIG. 4 is an X-ray powder diffraction pattern of topotecan hydrochloride crystalline Form II prepared according to Example 4.

16. Crystalline topotecan hydrochloride Form II having an X-ray powder diffraction pattern substantially as shown in FIG. 4.

17. The topotecan hydrochloride of claim 15, being prepared by a process comprising providing a solution of topotecan hydrochloride in water and removing water from the solution by co-distilling with an organic solvent.

18. The topotecan hydrochloride of claim 17, prepared by a process further comprising crystallizing topotecan hydrochloride from an organic solvent solution.

19. The topotecan hydrochloride of claim 15, containing about 0.001% to about 0.15% by weight of a compound having a formula:

20. Crystalline topotecan hydrochloride Form II having an X-ray power diffraction pattern comprising characteristic peaks at about 7.4, 7.9, 10.1, 19.7, 24.0, 25.0, 25.9, 27.1, and 27.9 ±0.20 degrees 2θ.

21. Crystalline topotecan hydrochloride having an X-ray power diffraction pattern comprising characteristic peaks at about 12.1 and 23.5 ±0.2 degrees 2 theta.

22. Crystalline topotecan hydrochloride Form I having an X-ray power diffraction pattern substantially as shown in FIG. 1.

23. Crystalline topotecan hydrochloride Form I having an X-ray power diffraction pattern comprising characteristic peaks at about 6.1, 12.1, 14.2, 22.9, 23.5, and 26.8 ±0.20 degrees 2θ.

24. The topotecan hydrochloride of claim 21, containing about 0.001% to about 0.15% by weight of a compound having a formula:

25. The crystalline topotecan hydrochloride as in any one of claims 15, 16, 20, 21, 22, and 23, having a purity as measured by HPLC of about 99.5% or more and having less than about 0.15% of any of

Formula II

Formula IV

Formula VI and

Formula VII

26. The process of claim 1, wherein said step of reacting 10-hydroxy camptothecin with dimethylamine and formaldehyde is conducted at a temperature of about 30 to about 60 degrees C.

27. The process of claim 1, wherein said step of reacting 10-hydroxy camptothecin with dimethylamine and formaldehyde is carried out for a time of between about 1 and about 10 hours.

28. The process of claim 1, wherein said step of reacting 10-hydroxy camptothecin with dimethylamine and formaldehyde is conducted at a temperature of about 30 to about 60 degrees C. and for a time of between about 1 and about 10 hours.

* * * * *